United States Patent
Kim et al.

(10) Patent No.: US 8,703,748 B2
(45) Date of Patent: Apr. 22, 2014

(54) CLEANING COMPOSITION FOR TREATING TISSUE FOR TRANSPLANTATION DERIVED FROM HUMAN/ANIMAL

(75) Inventors: Byoung Suck Kim, Seoul (KR); Seok Beom Song, Gyeonggi-do (KR); Goo Won Jeong, Seoul (KR); Hyo Jung Kang, Daegu (KR); Jae Deuck Jung, Seodaemun-gu (KR)

(73) Assignee: CG BIO Co., Ltd., Kyunggi-Do (KR)

( * ) Notice: Subject to any disclaimer, the term of this patent is extended or adjusted under 35 U.S.C. 154(b) by 217 days.

(21) Appl. No.: 13/148,555

(22) PCT Filed: Feb. 10, 2010

(86) PCT No.: PCT/KR2010/000813
§ 371 (c)(1),
(2), (4) Date: Aug. 9, 2011

(87) PCT Pub. No.: WO2010/093163
PCT Pub. Date: Aug. 19, 2010

(65) Prior Publication Data
US 2011/0312917 A1    Dec. 22, 2011

(30) Foreign Application Priority Data
Feb. 11, 2009    (KR) ........................ 10-2009-0010866

(51) Int. Cl.
| | |
|---|---|
| A01N 57/10 | (2006.01) |
| A61K 31/66 | (2006.01) |
| A01N 37/02 | (2006.01) |
| A61K 31/23 | (2006.01) |
| A01N 31/00 | (2006.01) |
| A61K 31/045 | (2006.01) |

(52) U.S. Cl.
USPC ........................ 514/144; 514/552; 514/724

(58) Field of Classification Search
USPC .................... 514/144, 552, 724; 510/109
See application file for complete search history.

(56) References Cited

U.S. PATENT DOCUMENTS
6,024,735 A * 2/2000 Wolfinbarger, Jr. ........... 604/500

FOREIGN PATENT DOCUMENTS
| | | | |
|---|---|---|---|
| KR | 20060036901 | * | 10/2006 |
| WO | WO 02096931 | | 12/2002 |
| WO | WO 2004099384 | * | 11/2004 |
| WO | WO 2008039021 | | 4/2008 |

OTHER PUBLICATIONS
Jones (Int J of Pharmaceutics, 177, 1999, 137-159).*
English Abstract of Korean Patent Application Publication No. 10-2001-0044514, Jun. 5, 2001.
International Search Report of PCT/KR10/00813, Sep. 6, 2010.
International Preliminary Report on Patentability of PCT/KR10/00813, Aug. 16, 2011.

* cited by examiner

Primary Examiner — Sreeni Padmanabhan
Assistant Examiner — Uma Ramachandran
(74) Attorney, Agent, or Firm — Clark G. Sullivan; Troutman Sanders LLP

(57) ABSTRACT

The present invention relates to a cleaning composition for removing cellular components from tissue for transplantation derived from humans and animals. More particularly, the present invention relates to a cleaning composition for treating tissue for transplantation comprising a polyoxyethyleneglycol $C_{14}$-$C_{20}$alkyl ether as a first protein solubilizing component, a $C_6$-$C_8$alkylphenol polyethoxylate as a first lipid solubilizing component, a $C_{10}$-$C_{16}$alkyl glycoside as a second protein solubilizing component and a $C_9$-$C_{12}$alkylphenoxy polyethoxy ethanol as a second lipid solubilizing component.

5 Claims, 1 Drawing Sheet

CLEANING COMPOSITION FOR TREATING TISSUE FOR TRANSPLANTATION DERIVED FROM HUMAN/ANIMAL

TECHNICAL FIELD

The present invention relates to a cleaning composition for removing cellular components from tissue for transplantation derived from human/animal. More particularly, the present invention relates to a cleaning composition for treating tissue for transplantation comprising polyoxyethyleneglycol $C_{14}$-$C_{20}$alkyl ether as a first protein solubilizing component, $C_6$-$C_8$alkylphenol polyethoxylate as a first lipid solubilizing component, $C_{10}$-$C_{16}$alkyl glycoside as a second protein solubilizing component and $C_9$-$C_{12}$alkylphenoxy polyethoxy ethanol as a second lipid solubilizing component.

BACKGROUND ART

When a part of tissue of body is impaired due to trauma, infection, tumor, degenerative disease, congenital disease, etc., autograft transplantation can be performed as a treating method. Autograft transplantation has a variety of advantages over allograft transplantation but has some problems as follows: requirement of more time from 30 minutes to 1 hour in operation and anesthesia for obtaining autograft tissue and suture; pain, bleeding and complication such as infection which may occur in the tissue-providing region; limitation of available graft tissue; and irregularity of tissue shape. Recently, as medical technology has developed, the demand for tissue transplantation materials is increasing in many fields such as orthopedics, neurosurgery, plastic surgery, general surgery, thoracic surgery, etc. As a result, allograft and xenograft transplantations are increasing in substitution for autograft tissue transplantation.

In allograft and xenograft tissue transplantations, two problems are intrinsically entailed. One is the possibility that infectious diseases or cancer may be propagated from a donor to a donee via transplantation materials. The other is the possibility that immune rejection response in a donee may be caused by foreign proteins or adipocytes.

Regarding the propagation of infectious diseases, it has been reported that pathogenic bacteria, fungi, virus and cancer cell are propagated from a donor to a donee via tissue transplantation. More particularly, regarding bacteria infection of donee after allograft transplantation, 1 case in 1953, 1 case in 1981, 3 cases in 1988, 1 death case in 2002, 1 case in 2003, 14 cases in sports medicine between 1988 and 2002, and 2 cases in 2006 have been reported in the U.S.A. In addition, after allograft transplantation, there was 1 case of hepatitis type B in 1954; 1 case in 1992, 2 cases in 1995; 4 cases in 2005 of hepatitis type C; 1 case in 1988, 3 cases in 1992 of acquired immunodeficiency syndrome (AIDS); *Candida albicans* infection in 1996; and bovine spongiform encephalopathy (BSE) infections after allograft corneal or epidural transplantation in 1974, 1981, 1987 and 1991 were reported to the U.S. CDC (Centers for Disease Control and Prevention). In case of allograft, the infectious propagation to donees has been considerably decreased by strict selection of donors; medical, social, sexual history inspection; physical test, inspection for medical record and donor serum, etc. However, infectious diseases can still be propagated because virus may not be detected in a general donor serum test if the test is conducted during the "window period," which is the time between viral infection and generation of antibodies, or the virus is a new virus such as Severe Acute Respiratory Syndrome (SARS) coronavirus or Avian Influenza virus. Thus, in the case of using a fresh allograft or a xenograft tissue for treating the human body, the sterilization step of tissue for transplantation is absolutely required to prevent infection or cancer propagation.

Besides propagation of infectious diseases, immune rejection response after allograft or xenograft transplantation is also problematic. After tissue transplantation is performed, various cell groups existing in the transplanted material, and other materials remaining in bone such as collagen, ground substance, proteoglycan, link protein, inorganic minerals, etc. are involved in immune rejection response. They exist on the surface membrane glycoprotein of cells such as bone cells, chondrocytes, fibrous cells, vascular cells, adipocytes, nerve cells, stem cells, etc. Among the cells involved in immune rejection response in bone, leukocytes, myelocytes and adipocytes are removable without changing the structure or nature of the bone. These cell groups have a close relation to immune rejection response. Therefore, in order to increase the engraftment rate in the donee's body after allograft or xenograft transplantation and to minimize immune rejection response, such cell groups must be removed from bone as much as possible.

Tissue for transplantation can be disinfected initially by washing. The tissue may be washed by physical processing, for example, such as simple washing, centrifuge, pasteurization or sonification, etc., or by chemical processing of using various solvents, for example, such as ethanol, methanol, chloroform, iodoacetic acid, peracetic acid-ethanol, sodium hypochloride, ethylene diamine, glycerol, hydrogen peroxide, etc. However, the efficacy of each method has not yet been studied and reported sufficiently. Conventional chemical treating processes use one kind of chemical alone. Recently, the use of a combination of several kinds of chemicals has been studied to increase the efficacy.

When using one kind of chemical alone, only one kind of lipid or protein is washed, or only fraction of the bacteria or viruses existing in infected tissue are inactivated. Thus, a method of increasing the washing efficiency by properly combining the components of washing solution is needed to inactivate bacteria and viruses by destroying membranes of various cells such as bone marrow cells, erythrocytes and leukocytes.

Therefore, there has been an increased demand for a cleaning solution useful in chemical processing to minimize infection with bacteria, prions via transplanted tissue, and bone marrow cells, leukocytes, adipocytes, etc. which are known to be directly involved in immune rejection response. If such a cleaning solution is used, the infection of transplantation graft can be decreased and the engraftment rate can be improved with the use of a tissue treated by the solution in allograft or xenograft transplantation.

DISCLOSURE OF INVENTION

The object of the present invention is to provide a novel cleaning composition for treating tissue for transplantation, which is more effective than a conventional cleaning composition used for chemically treating process of tissue for transplantation in removing bacteria or viruses, removing bone marrow cells, leukocytes and adipocytes acting as antigens, thus decreasing the immune rejection response of graft, and minimizing the change of biomechanical properties or biological characteristics.

To accomplish the above object, the present invention provides a cleaning composition for treating tissue for transplantation comprising polyoxyethyleneglycol $C_{14}$-$C_{20}$alkyl ether as a first protein solubilizing component, $C_6$-$C_8$alkylphenol polyethoxylate as a first lipid solubilizing component, $C_{10}$-$C_{16}$alkyl glycoside as a second protein solubilizing component and $C_9$-$C_{12}$alkylphenoxy polyethoxy ethanol as a second lipid solubilizing component.

MODE FOR THE INVENTION

Figure 1:
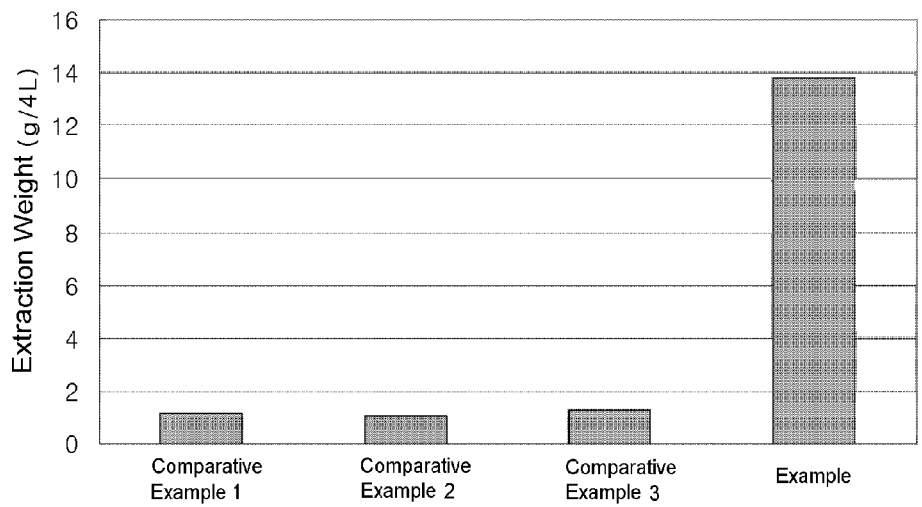
FIG. 1 is a graph representing the results of crude lipid extraction in the Example and Comparative Examples.

The present invention is described in detail hereinafter.

In the cleaning composition of the present invention, if polyoxyethyleneglycol alkyl ether having the alkyl moiety with a carbon number below 14 or above 20 is used as the first protein solubilizing component, the cleaning efficacy, specifically removing efficacy of crude lipid in object tissue, may be deteriorated. In the cleaning composition of the present invention, the first protein solubilizing component is preferably polyoxyethyleneglycol $C_{15}$-$C_{18}$alkyl ether, and more preferably polyoxyethylene glycol hexadecyl (i.e., $C_{16}$alkyl) ether such as Brij 58 (trademark).

In the cleaning composition of the present invention, the first lipid solubilizing component is $C_6$-$C_8$alkylphenol polyethoxylate, preferably $C_7$-$C_8$alkylphenol polyethoxylate, and more preferably $C_8$alkylphenol polyethoxylate such as Triton X-100 (trademark).

In the cleaning composition of the present invention, the second protein solubilizing component is $C_{10}$-$C_{16}$alkyl glycoside, preferably $C_{11}$-$C_{14}$alkyl glycoside, and more preferably $C_{12}$alkyl glycoside such as n-dodecyl-β-D-maltoside.

In the cleaning composition of the present invention, the second lipid solubilizing component is $C_9$-$C_{12}$alkylphenoxy polyethoxy ethanol, preferably $C_9$-$C_{10}$alkylphenoxy polyethoxy ethanol, and more preferably $C_9$alkylphenoxy polyethoxy ethanol such as Triton N-101 (trademark).

According to the present invention, the cleaning composition for treating tissue for transplantation comprising polyoxyethyleneglycol $C_{14}$-$C_{20}$alkyl ether as the first protein solubilizing component, $C_6$-$C_8$alkylphenol polyethoxylate as the first lipid solubilizing component, $C_{10}$-$C_{16}$alkyl glycoside as the second protein solubilizing component and $C_9$-$C_{12}$alkylphenoxy polyethoxy ethanol as the second lipid solubilizing component is provided. In the above composition, the content ratio of the first protein solubilizing component:the first lipid solubilizing component:the second protein solubilizing component:the second lipid solubilizing component is preferably 1:0.05-1.5:0.2-2:0.05-1.5, more preferably 1:0.2-1.0:0.5-1.5:0.2-1.0, and still more preferably 1:0.4-0.8: 0.8-1.2:0.4-0.8, as a weight ratio. If the content ratio of the first protein solubilizing component:the first lipid solubilizing component:the second protein solubilizing component: the second lipid solubilizing component is out of the above range, cleaning efficacy may be deteriorated. The cleaning composition of the present invention most preferably comprises $C_{16}$alkyl ether:$C_8$alkylphenol polyethoxylate:$C_{12}$alkyl glycoside:$C_9$alkylphenoxy polyethoxy ethanol as the weight ratio of 1.75:1:1.75:1.

To be used as a cleaning solution for treating tissue for transplantation, the cleaning composition of the present invention may be diluted such as with water, preferably deionized water or distilled water. There is no limitation in dilution ratio. For example, the cleaning composition of the present invention may be diluted 10 times to 1,000 times, but it is not limited thereto.

The cleaning composition of the present invention or a cleaning solution comprising the same may further comprises one or more bactericidal or anti-viral components such as ethanol, tri(n-butyl)phosphate (TNBP), fatty acid ester such as Polyxyl 40 stearate (trademark), etc. to increase bacteria or virus inactivation efficacy. Ethanol has a bactericidal effect on some Gram-positive bacteria (*Mycobacterium tuberculosis, Chlamydia*, etc.) and some Gram-negative bacteria (*Yersinia enterocolitica* etc.). TNBP and fatty acid ester are known to have anti-viral effects. There is no specific limitation on the content of such an additional bactericidal or anti-viral component. They may be properly added within a range in which the object of the present invention can be obtained, if necessary.

According to the present invention, a novel cleaning composition for treating tissue for transplantation, which is more effective than a conventional cleaning composition used for chemically treating process of tissue for transplantation in removing bacteria or viruses, removing bone marrow cells, leukocytes, adipocytes acting as antigens, thus decreasing the immune rejection response of graft and minimizing the change of biomechanical properties or biological characteristics can be obtained.

Hereinafter, the present invention is explained in more detail with the following examples. However, it must be understood that the protection scope of the present invention is not limited to the examples.

EXAMPLE 100 mL (10× concentration) of cleaning composition was prepared by mixing 0.35 g of polyoxyethylene glycol hexadecyl ether (trademark: Brij 58), 0.2 g of 4-octylphenol polyethoxylate (trademark: Triton X-100), 0.35 g of n-dodecyl-β-D-maltoside and 0.2 g of nonyl phenoxy polyethoxy ethanol (trademark: Triton N-101) (weight ratio of 1.75:1: 1.75:1) with distilled water.

10 g of TNBP (1 wt %) and 5 g of polyxyl 40 stearate (0.5 wt %) were added to 1 mL of the prepared cleaning composition, and then it was diluted with ethanol solution to obtain 1,000 mL of cleaning solution with a final ethanol concentration of 10% for treating tissue for transplantation.

Comparative Examples 1 to 3

As cleaning solutions for treating tissue for transplantation, distilled water (Comparative Example 1), normal saline (Comparative Example 2) and solution A (Comparative Example 3) were prepared. Solution A was prepared according to the method disclosed in the example of U.S. Pat. No. 5,977,034 by mixing polyethylene(23) lauryl ether (trademark: Brij 35), nonylphenoxypolyethoxyethanol (trademark: Tergitol NP-40) and nonylphenyl polyethylene glycol ether (trademark: Nonoxynol-9) in a weight ratio of 3.3:1:1.

Experiment 1

A pig's humerus bone (160 g) was used as experimental material. The experiment was carried out in decaplicate per each cleaning solution under the same condition (solution temperature: 40° C., final volume: 4 L, 50 psi). The experimental protocol was as follows:

(1) Soft tissue and cartilage of a pig's humerus bone were removed by using a raspatory and a surgeon's knife.

(2) The humerus bone was cut so that the weight of the part including the proximal part of the humerus bone was the same.

(3) A tapping port was inserted into a marrow cavity of the humerus bone, and then the periphery of insertion was sealed with parafilm.

(4) A cleaning solution was prepared in a 20 L carboy.

(5) The cleaning solution was heated to 40° C. in a container having good thermal conductivity.

(6) A reactor was prepared.

(7) The cleaning solution, which was heated to 40° C., was injected into the reactor and a cleaning bottle.

(8) The tapping port connected to the marrow cavity of the humerus bone was connected to a hose connected to the input of a pump.

(9) The marrow cavity of the humerus bone connected to the hose and output hose of the pump were inserted into the reactor.

(10) The pump was operated at 50 psi pressure.

(11) Pumping was carried out for 15 minutes and then stopped.

(12) The humerus bone was removed from the reactor.

(13) The tapping port was disconnected from the hose.

(14) Input and output hoses of the pump were inserted into the reactor, and then the pump was operated.

(15) After 2-3 minutes, the input hose was removed from the reactor.

(16) All of the solution remaining in the hose was delivered to the reactor.

(17) The solution in the reactor was transferred to another container.

(18) The extract on the surface of the reactor was washed with cleaning solution, and then the resulting solution was added to the solution retrieved from the reactor.

(19) The solution was heated in 40° C. thermostatic water bath to maintain a homogeneous concentration of lipid of the reaction extract.

(20) After heating for 20-30 minutes, the solubilized reaction extract was aliquoted into sample vials.

(21) After mixing by shaking the sample vials, an analysis sample was taken from the sample vials.

(22) The sample vials and analysis samples were stored in a refrigerator.

Crude lipid of the sample stored in the refrigerator was analyzed by an acid hydrolysis method. The analysis results of the crude lipid extraction are shown in Table 1, and represented in FIG. 1 as a graph (extraction result is a mean of 10 samples).

TABLE 1

| Test Item | Example | Comparative Example 1 | Comparative Example 2 | Comparative Example 3 |
|---|---|---|---|---|
| Crude lipid (g/4 L) | 13.840 | 1.160 | 1.067 | 1.314 |

As can be seen in Table 1, 11.93 times as much crude lipid was extracted in the Example than in Comparative Example 1 (distilled water) and 12.97 times as much in Comparative Example 2 (normal saline), both of which are negative controls.

Furthermore, 10.53 times as much crude lipid was extracted in the Example than in Comparative Example 3 (solution A).

Experiment 2

Figure 2:
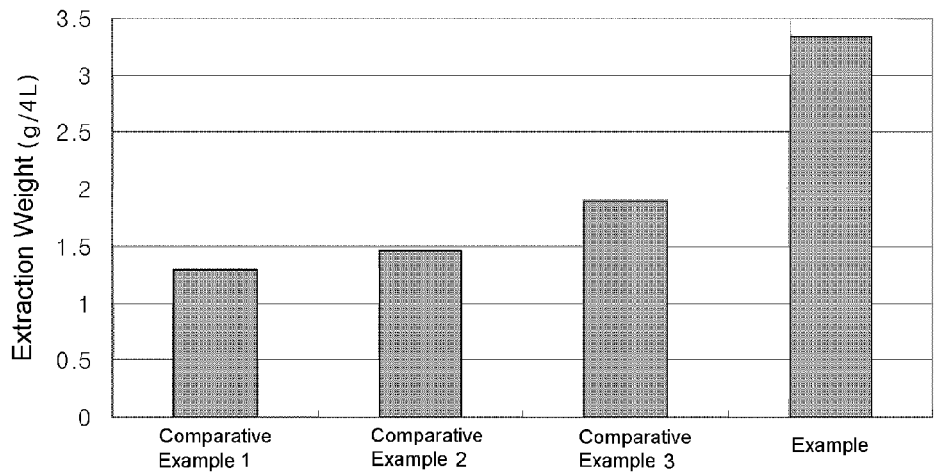
FIG. 2 is a graph representing the results of crude protein extraction in the Example and Comparative Examples.

Crude protein of the sample stored in the refrigerator was analyzed by using a BCA kit. The analysis results of the crude protein extraction are shown in Table 2, and represented in FIG. 2 as a graph (extraction result is a mean of 10 samples).

TABLE 2

| Test Item | Example | Comparative Example 1 | Comparative Example 2 | Comparative Example 3 |
|---|---|---|---|---|
| Crude protein (g/4 L) | 3.332 | 1.3 | 1.451 | 1.890 |

As can be seen in Table 2, 2.56 times as much crude protein was extracted in the Example than in Comparative Example 1 (distilled water) and 2.30 times as much in Comparative Example 2 (normal saline), both of which are negative controls.

Furthermore, 1.76 times as much crude protein was extracted in the Example than in Comparative Example 3 (solution A).

From the above results, it can be known that the cleaning solution according to the present invention has an excellent ability to remove bacteria, viruses, etc. compared with the conventional solution A by means of exposing constitutional components by solubilizing protein and lipid in the membrane of cells such as bone marrow cells, leukocytes, erythrocytes and platelets which may be potentially infected by new viruses (SARS, Avian Flu virus, etc.) or during the "window period," when viral infection cannot be detected.

Therefore, when the cleaning solution according to the present invention is used in treating tissue for transplantation, the inflammatory reaction of graft tissue caused by lipid is minimized because of the excellent extraction effect of crude protein and crude lipid. In addition, immune rejection response is minimized as much as possible by the removal of cells in bone.

The invention claimed is:

1. A cleaning composition for treating tissue for transplantation comprising:
polyoxyethyleneglycol $C_{14}$-$C_{20}$alkyl ether as a first protein solubilizing component, $C_6$-$C_8$alkylphenol polyethoxylate as a first lipid solubilizing component, $C_{10}$-$C_{16}$alkyl glycoside as a second protein solubilizing component, $C_9$-$C_{12}$alkylphenoxy polyethoxy ethanol as a second lipid solubilizing component, and alcohol or fatty acid ester as a bactericidal or an anti-viral component, wherein a content ratio of $C_{14}$-$C_{20}$alkyl ether:$C_6$-$C_8$alkylphenol polyethoxylate:$C_{10}$-$C_{16}$alkyl glycoside:$C_9$-$C_{12}$alkylphenoxy polyethoxy ethanol is 1:0.05-1.5:0.2-2:0.05-1.5 as a weight ratio.

2. The cleaning composition according to claim 1, wherein the first protein solubilizing component is polyoxyethyleneglycol $C_{16}$alkyl ether.

3. The cleaning composition according to claim 1, wherein the first lipid solubilizing component is $C_8$alkylphenol polyethoxylate.

4. The cleaning composition according to claim 1, wherein the second protein solubilizing component is $C_{12}$alkyl glycoside.

5. The cleaning composition according to claim 1, wherein the second lipid solubilizing component is $C_9$alkylphenoxy polyethoxy ethanol.

* * * * *